United States Patent
Horii

(10) Patent No.: US 9,523,644 B2
(45) Date of Patent: Dec. 20, 2016

(54) METHOD AND APPARATUS FOR DETECTING A TRENCH CREATED IN A THIN FILM SOLAR CELL

(71) Applicant: MITSUBOSHI DIAMOND INDUSTRIAL CO., LTD., Osaka (JP)

(72) Inventor: Ryogo Horii, Osaka (JP)

(73) Assignee: MITSUBOSHI DIAMOND INDUSTRIAL CO., LTD., Osaka (JP)

( * ) Notice: Subject to any disclaimer, the term of this patent is extended or adjusted under 35 U.S.C. 154(b) by 0 days.

(21) Appl. No.: 14/555,190

(22) Filed: Nov. 26, 2014

(65) Prior Publication Data

US 2015/0185162 A1 Jul. 2, 2015

(30) Foreign Application Priority Data

Dec. 27, 2013 (JP) ................. 2013-271656

(51) Int. Cl.
| | | |
|---|---|---|
| G01J 5/02 | (2006.01) | |
| G01N 21/84 | (2006.01) | |
| G01N 21/95 | (2006.01) | |
| H01L 31/0463 | (2014.01) | |

(52) U.S. Cl.
CPC ...... *G01N 21/8422* (2013.01); *G01N 21/9505* (2013.01); *H01L 31/0463* (2014.12); *G01N 2201/105* (2013.01); *Y02E 10/541* (2013.01)

(58) Field of Classification Search
CPC ........ G01J 3/42; G01J 5/34; G01J 2005/0077; G01N 21/35; G01N 25/72
USPC ..... 250/261, 269.1, 299, 334, 338, 582, 586
See application file for complete search history.

(56) References Cited

U.S. PATENT DOCUMENTS

| | | | | |
|---|---|---|---|---|
| 2005/0239223 A1* | 10/2005 | Mantz | .................. | G01N 21/55 438/14 |
| 2010/0074515 A1* | 3/2010 | Zhao et al. | .................. | 382/149 |
| 2010/0233386 A1* | 9/2010 | Krause | ........... | H01L 31/022425 427/596 |
| 2011/0179934 A1* | 7/2011 | Soyama | ......................... | 83/875 |
| 2014/0110582 A1* | 4/2014 | Marx et al. | .............. | 250/339.08 |

FOREIGN PATENT DOCUMENTS

| | | |
|---|---|---|
| JP | 11-312815 A | 11/1999 |
| JP | 2002-94089 A | 3/2002 |
| JP | 2004-115356 A | 4/2004 |

* cited by examiner

*Primary Examiner* — David Porta
*Assistant Examiner* — Mamadou Faye
(74) *Attorney, Agent, or Firm* — McDermott Will & Emery LLP

(57) ABSTRACT

A method and an apparatus for precisely detecting a trench S in a product W to become a thin film solar cell are provided. In the product W, a lower electrode layer 12, in which the trench S is created, and light absorbing layers 13 and 14 are layered on a substrate 11 in this order. The method includes the steps of: detecting infrared rays for imaging, of which the wavelengths are in such a range that can transmit through the light absorbing layers 13 and 14 and which are irradiated from the product W, by means of an infrared ray imaging apparatus 16 that is provided above the light absorbing layers 13 and 14 so that image data for radiation intensity distribution can be taken; and detecting the trench S in the lower electrode layer 12 on the basis of this image data for radiation intensity distribution.

8 Claims, 5 Drawing Sheets

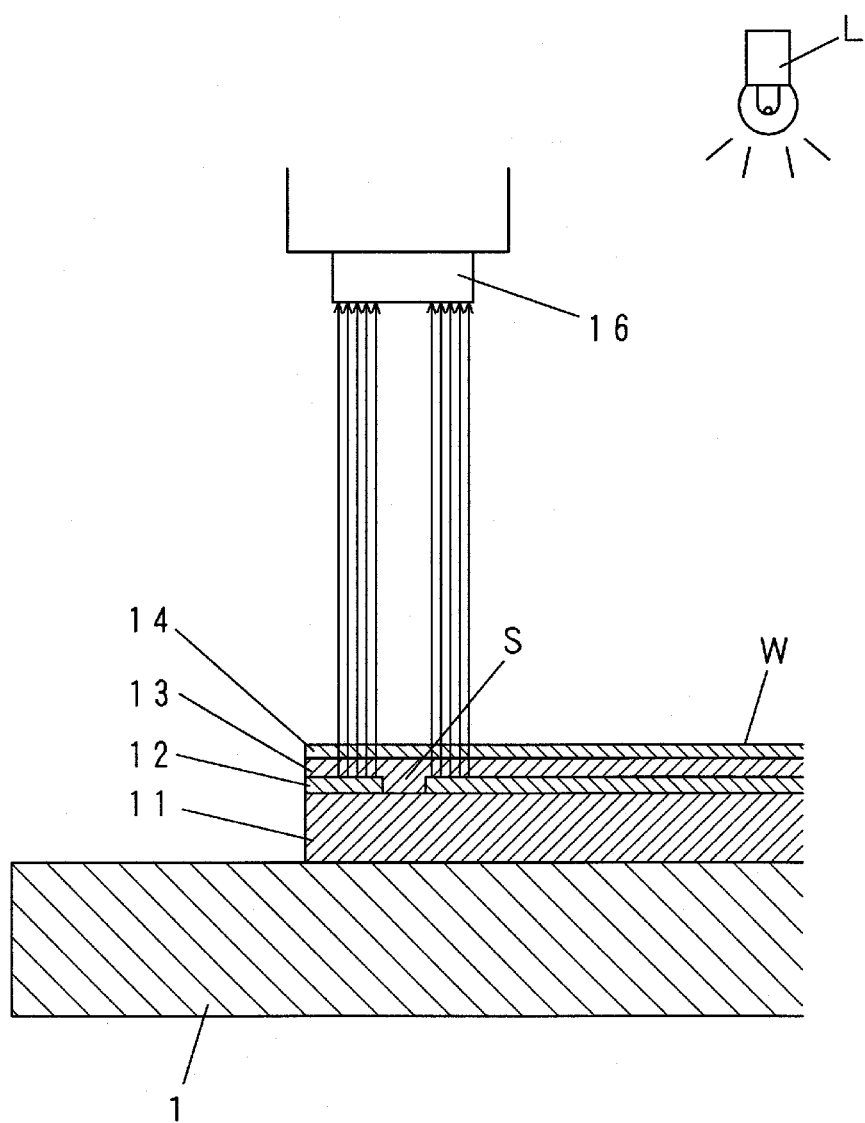

METHOD AND APPARATUS FOR DETECTING A TRENCH CREATED IN A THIN FILM SOLAR CELL

CROSS-RELATED TO RELATED APPLICATIONS

This Applicaton claims priority to Japanese Patent Application No. 2013-271656 filed Dec. 27, 2013, the subject matter of which is incorporated herein by reference in entirety.

BACKGROUND OF THE INVENTION

1. Field of the Invention

The present invention relates to a method for detecting a trench created in an integrated thin film solar cell using a compound semiconductor, such as a chalcopyrite compound, and an apparatus for detecting a trench created in a thin film solar cell used for the same.

Here, the chalcopyrite compound includes CIGSS (Cu(In, Ga)(Se, S)$_2$) and CIS (CuInS$_2$) in addition to CIGS (Cu(In, Ga)Se$_2$).

2. Description of Related Art

Thin film solar cells, which use a compound semiconductor for a light absorbing layer, generally have an integration-type structure where a number of unit cells are connected in series on a substrate.

A conventional method for manufacturing a chalcopyrite compound-based integrated-type thin film solar cell is described below. FIGS. 5(a) to 5(c) are diagrams showing the manufacturing steps thereof.

First, as shown in FIG. 5(a), an Mo electrode layer 12, which becomes a lower electrode on the plus side, is layered on an insulating substrate 11 made of solder lime glass (SLG) or the like, and then, a trench S for separating a lower electrode is created through a scribing process.

After that, as shown in FIG. 5(b), a light absorbing layer 13 made of a compound semiconductor (CIS) thin film is layered on the Mo electrode layer 12, and on top of this, a buffer layer 14 made of a ZnS thin film or the like is layered for a heterojunction. This buffer layer 14 essentially forms a part of the light absorbing layer 13. Subsequently, a trench M1 for the inter-electrode contact that reaches the Mo electrode layer 12 is created through a scribing process in a location that is away from the trench S by a predetermined distance in the lateral direction so as to be parallel to the trench S.

Next, as shown in FIG. 5(c), a transparent electrode layer 15 is formed on the buffer layer 14 as an upper electrode made of a ZnO:Al thin film, and a trench M2 for separating an electrode that reaches the Mo electrode layer 12 below is created through a scribing process so as to be parallel to the trench M1.

In the above-described steps of manufacturing an integrated-type thin film solar cell, a laser scribing method using a laser beam, as disclosed in Patent Document 1, and a mechanical scribing method using a trench creating tool having a blade at the front, as disclosed in Patent Documents 2 and 3, for example, are used as the technology for creating a trench through scribing.

PRIOR ART DOCUMENTS

Patent Documents

Patent Document 1: Japanese Unexamined Patent Publication H11 (1999)-312815

Patent Document 2: Japanese Unexamined Patent Publication 2002-094089

Patent Document 3: Japanese Unexamined Patent Publication 2004-115356

SUMMARY OF THE INVENTION

1. Problem to be Solved by the Invention

In order to obtain high quality solar cells having high power generation efficiency, it is important to secure an area as wide as possible of the regions that are effective for power generation. In order to do so, it is effective to create a trench M1 for inter-electrode contact to be parallel to the trench S for isolating the lower electrode that has been previously processed in such a location as to be away from the trench S by a predetermined distance, which reduces loss in the area of the power generation regions. After the creation of the trench M1, a trench M2 is created parallel to the trench M1. Therefore, it is desirable to observe the trench S that has been created in the previous process so that the trench S can be used as a standard instead of an alignment mark that has been provided on the solar cell substrate in advance for positional adjustment when the position is adjusted before creating the trench M1 by means of a camera provided above the substrate.

As shown in FIG. 5(b), however, a light absorbing layer 13 made of a compound semiconductor, such as CIS, and a buffer layer 14 are layered above the trench S at the point in time when the trench M1 is being created. Though the light absorbing layer 13 has a thickness of approximately 1 μm, the layer absorbs solar light of which the wavelength ranges from visible light to near-infrared light (wavelength range: 0.3 μm to 1.4 μm) for photoelectric conversion, and therefore barely allows visible light to transmit through it. Accordingly, only an unclear image where the trench S in the Mo electrode layer 12 beneath the light absorbing layer 13 is hidden or slightly recognizable can be confirmed when the trench S is observed by means of an optical camera using visible light above the light absorbing layer 13.

Therefore, according to conventional methods used for creating the trench M1, the location of the trench S, which is slightly recognizable, is roughly detected from the unclear image, or the distance between the trench S and the trench M1 to be created has been determined in advance in accordance with the design so that the scribing process is mechanically carried out for this determined distance without confirming the image. However, an error in the location of the trench M1 or an error in the angle relative to the direction parallel to the trench S cannot be prevented from being made due to an error in the distance of movement of each drive unit in the scribing apparatus, an error in the positioning of the solar cell substrate relative to the table, or the effects of displacement factors, such as a bending of the substrate.

In the case where a glass substrate that allows visible light to transmit through it is used as the insulating substrate 11, measurement is possible through glass by means of an optical camera from the substrate 11 side according to another method. However, the thickness of the glass substrate to be used is 1 mm or greater (1.8 mm, for example), and therefore, an error in the refraction that is too great to be ignored (for example, an error of approximately 5 μm for the inclination of 0.5 degrees relative to the direction perpendicular to the surface of the substrate) is made when the optical axis is inclined due to a bending of the substrate.

Though it is also possible to observe the trench S from the substrate 11 side (rear surface side) by means of an overhead optical camera by flipping over the substrate, the substrate must again be flipped over in order to create the trench M1 in the light absorbing layer 13 after the observation by flipping over the substrate. Therefore, such a problem arises that a mechanism for flipping the table on which the substrate 11 is mounted becomes necessary, which makes the unit complicated, larger scaled, and more expensive.

In the case where the insulating substrate 11 is made of a metal or a resin that does not allow visible light to transmit through it, by definition, the trench S cannot be observed from the substrate 11 side.

Therefore, an object of the present invention is to provide a new method for detecting a trench according to which a trench S for separating a lower electrode that has already been created beneath the light absorbing layer can be precisely detected, as well as to provide an apparatus for detecting a trench used in this method.

2. Means for Solving Problem

In the method for detecting a trench created in a product to become a thin film solar cell according to the present invention that has been provided in order to achieve the above-described object, a lower electrode layer and a light absorbing layer are layered on a substrate in this order, and at the same time, a trench for separating a lower electrode is created in a portion of the above-described lower electrode layer, and the above-described trench is covered by the above-described light absorbing layer, infrared rays for imaging, of which the wavelengths are in such a range that can transmit through the above-described light absorbing layer and which are irradiated from the above-described product, are detected by means of an infrared ray imaging apparatus that cannot detect visible light but detects infrared rays for imaging and is provided above the above-described light absorbing layer so that image data for radiation intensity distribution of infrared rays for imaging can be taken, and the trench in the above-described lower electrode layer is detected on the basis of the above-described image data for radiation intensity distribution.

In the apparatus for detecting a trench created in a product to become a thin film solar cell according to the present invention that has been provided from another aspect, a lower electrode layer and a light absorbing layer are layered on a substrate in this order, and at the same time, a trench for separating a lower electrode is created in a portion of the above-described lower electrode layer, and the above-described trench is covered by the above-described light absorbing layer, and the apparatus for detecting a trench created in a product to become a thin film solar cell has a table on which the above-described product is mounted with the above-described light absorbing layer facing up, an infrared ray imaging apparatus, which is provided above the above-described table, which does not detect visible light but detects infrared rays for imaging of which the wavelengths are in such a range that can transmit through the above-described light absorbing layer, and which acquires image data of the radiation intensity distribution of the infrared rays for imaging, and a baseline determining unit for detecting the trench in the lower electrode layer on the basis of the above-described image data of the radiation intensity distribution.

3. Effects of the Invention

Materials that efficiently absorb the visible light that is found in large amounts in solar light are selectively used for the light absorbing layer in a thin film solar cell in order to increase the efficiency in photoelectric conversion. Therefore, trenches created in a lower electrode layer located beneath the light absorbing layer are not visible because most of the visible light is absorbed when passing through the light absorbing layer, and thus cannot transmit through the light absorbing layer. However, infrared rays having wavelengths that are in such a range as to not be absorbed by the light absorbing layer can transmit through the light absorbing layer. In the present specification, light having wavelengths that are in such a range as to not be absorbed by the light absorbing layer is referred to as infrared rays for imaging. In chalcopyrite-type solar cells, for example, light with a wavelength of 1.4 μm or greater transmits through the light absorbing layer without fail, and thus corresponds to infrared rays for imaging.

Meanwhile, the lower electrodes are formed of a metal (Mo, for example) that does not allow infrared rays to transmit through it, and absorbs part of the infrared rays while reflecting the rest of the infrared rays. Accordingly, when natural light that includes infrared rays or light from a fluorescent lamp or the like enters from the top, the infrared rays that have transmitted through the light absorbing layer and reached the lower electrode layer are absorbed by or reflected from the lower electrode layer, and thus again transmits through the light absorbing layer as radiation light so as to be emitted from the above as radiation infrared rays.

Thus, an infrared ray imaging apparatus that is not sensitive to visible light but is sensitive to radiation infrared rays (an infrared ray imaging apparatus for detecting infrared rays with a wavelength of 1.4 μm or greater, for example) is used to take an image of the regions in close proximity to the trench for separating a lower electrode created in a product to become a thin film solar cell. Then, the visible light reflected from the surface of the light absorbing layer (thin film) and the visible light absorbed by the light absorbing layer are not detected at all, while the radiation infrared rays (infrared rays for imaging) that have transmitted through the light absorbing layer, been absorbed by or reflected from the lower electrode layer, and have again transmitted through the light absorbing layer can be detected. The image data taken at this time shows the distribution of the intensity of the radiation infrared rays. In addition, the amount of the radiation infrared rays from the trench where no lower electrode layer exists is much smaller than that from the portions where the lower electrode layer exists, and thus, the trench is darker than the other portions in the images that have been taken. Accordingly, image data (thermography) showing the border between the lower electrode layer and the trench with a contrast between the brightness and darkness (difference in the brightness value) can be acquired.

A location where the brightness value changes greatly can be sampled from the thus-gained image data so that the location of the border between the trench and the electrode can be detected, and therefore, the locations of a pair of borders, left and right, can be detected so as to precisely determine the location and the direction of the trench to be created.

Therefore, according to the present invention, a border between the trench that has been created in the lower electrode layer and the lower electrode can be detected from the image data taken by an infrared ray imaging apparatus not having sensitivity to visible light but having sensitivity to radiation infrared rays, and as a result, such excellent effects can be gained that the location and the direction of the trench in the lower electrode layer that is hidden beneath the light absorbing layer can be precisely determined and used as a baseline.

Thus, this baseline makes it possible for a trench M1 to be created in the light absorbing layer parallel to the trench S in the lower electrode. As a result, such an effect can be gained that high quality thin film solar cells having excellent power generation efficiency by suppressing a loss in the power generation region can be manufactured.

DESCRIPTION OF THE DRAWINGS

FIG. 2 is a diagram showing a main portion of the apparatus for detecting a trench created in a thin film solar cell in FIG. 1;

DETAILED DESCRIPTION OF EMBODIMENTS

In the following, the embodiments of the present invention are described in detail in reference to the drawings.

Figure 1:
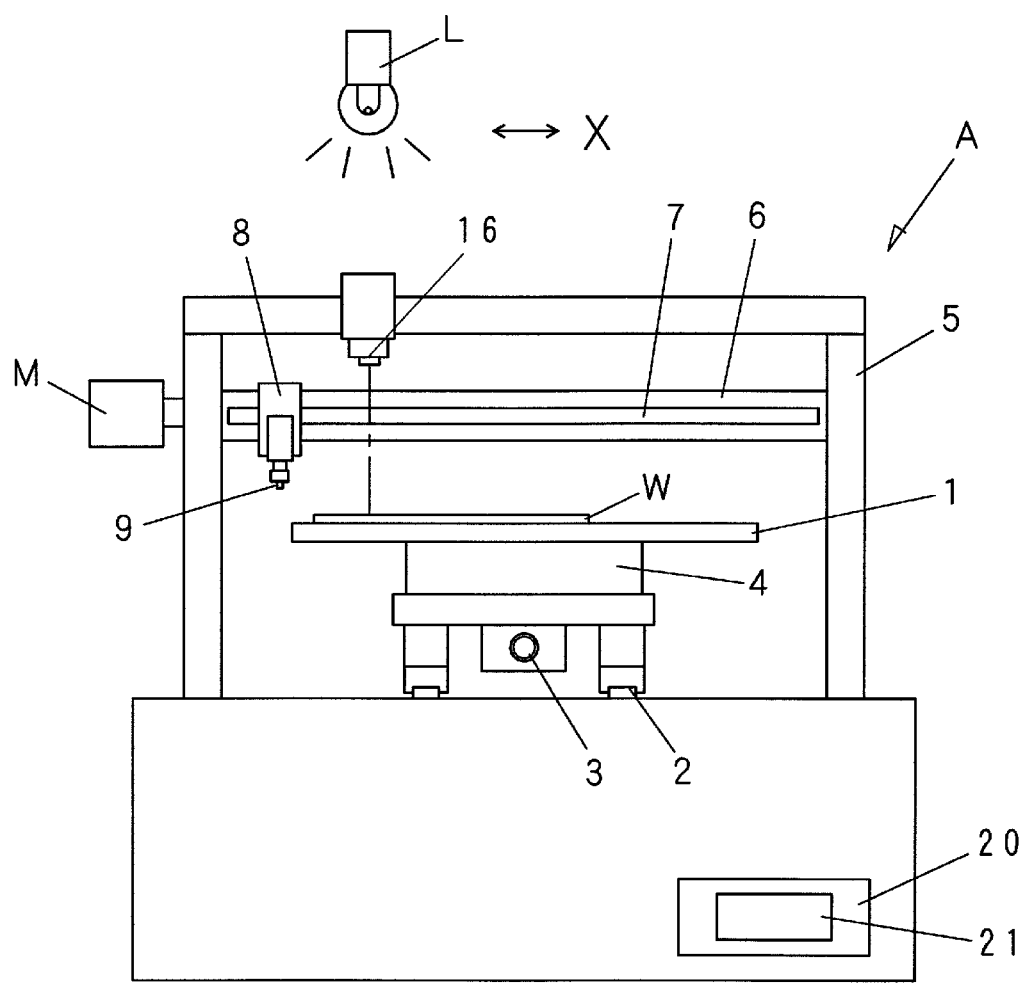
FIG. 1 is a schematic front diagram showing a thin film solar cell processing apparatus having an apparatus for detecting a trench created in a thin film solar cell according to one embodiment of the present invention.

FIG. 1 is a schematic front diagram showing an example of an apparatus for processing a thin film solar cell having an apparatus for detecting a trench created in a thin film solar cell according to the present invention. FIG. 2 is a diagram showing a main portion of the apparatus for detecting a trench created in a thin film solar cell.

An apparatus for detecting a trench created in a thin film solar cell A is provided with a table 1 for holding a product to become a solar cell W where thin film layers are layered on a glass substrate when the product to become a solar cell W is placed on the table 1. The table 1 is driven by a threaded axis 3 that is rotated by a motor (not shown), and thus can move in the direction Y (front and rear directions in FIG. 1) along horizontal rails 2. Furthermore, the table 1 can rotate within a horizontal plane by means of a rotation drive unit 4 with a built-in motor.

A horizontal beam 6 of a bridge 5 in gate shape provided so as to settle over the table 1 is provided with a guide 7 that extends in the X direction, and a scribing head 8 is attached to this guide 7 so as to be movable in the X direction by means of a motor M. Either of the following trench creating mechanisms is attached to this scribing head 8: a trench creating tool for creating a trench through mechanical scribing on the surface of the thin film of a product to become a solar cell (product to be processed) mounted on the table 1 or a laser emitting mechanism for creating a trench through thermal scribing. In the present embodiment, this trench creating mechanism attached to the scribing head 8 is a trench creating tool 9 having a blade with approximately the same width as the width of the trench M1 to be created in such a manner that the trench is created through peeling with the blade that is made to make contact with the thin film layer.

Thus, a control unit 20 formed of a computer controls the movement of the scribing head 8 in the X direction and the movement of the table 1 in the Y direction so that the movements are linked to each other, and therefore, a scribing process is made possible in any direction within the XY plane including diagonal directions.

An apparatus A for detecting a trench created in a thin film solar cell is used under such an environment that infrared rays of which the wavelength is in such a region that transmit the light absorbing layer in the product W to be processed (infrared rays for imaging) enter from the light absorbing layer side. Here, infrared rays included in natural light or an illumination L, such as a fluorescent lamp, are sufficient, and therefore, it is not necessary to provide a light source for emitting infrared rays for imaging, and thus, the apparatus A can be used unless it is put in such a place as a dark room that is not irradiated with infrared rays.

An infrared ray line scanning camera 16 is provided above the table 1 as an infrared ray imaging apparatus for sensing radiation infrared rays generated from the product W to be processed that is mounted on the table 1 as image data (thermography). This infrared ray line scanning camera 16 can detect infrared rays of which the wavelength is 1.4 μm or greater and in the region that transmits through the light absorbing layers 13 and 14 (infrared rays for imaging), and at the same time has such a sensitivity that visible light of which the wavelength is 1.4 μm or less (partially including infrared rays) cannot be detected, and thus, the detection range of wavelengths is limited. Concretely, a light path can be intervened with a filter for cutting light with a wavelength that is less than 1.4 μm so that the detection range can be easily gained. Alternatively, a spectrometric function may be provided to the infrared ray camera so that image data can be prepared using a wavelength of 1.4 μm or greater.

Thus, a product W to be processed is placed on the table 1 in such a position that one end of a trench S in the product W is located within a range of which the image can be taken by the infrared ray line scanning camera 16, and the respective points along the trench S come into the range of which the image can be taken by the infrared ray line scanning camera 16 when the table 1 is driven in the direction towards the trench S (Y direction, front to back direction in FIG. 1), and thus, images of the respective points along the trench S can be taken for image data.

The image data of the images that have been taken is sent to the control unit 20 made of a computer where images of the respective points are synthesized so that image data that includes the vicinity of the trench S can be prepared. Here, the control unit 20 is provided with a standard line determining unit 21 having such a function as to determine the precise position of the trench S on the basis of this image data. The standard line determining unit 21 carries out a statistic process, such as a digital filtering process and an averaging process, so that the location of a line along the center of the trench S can be determined from the image data.

Figure 3A:
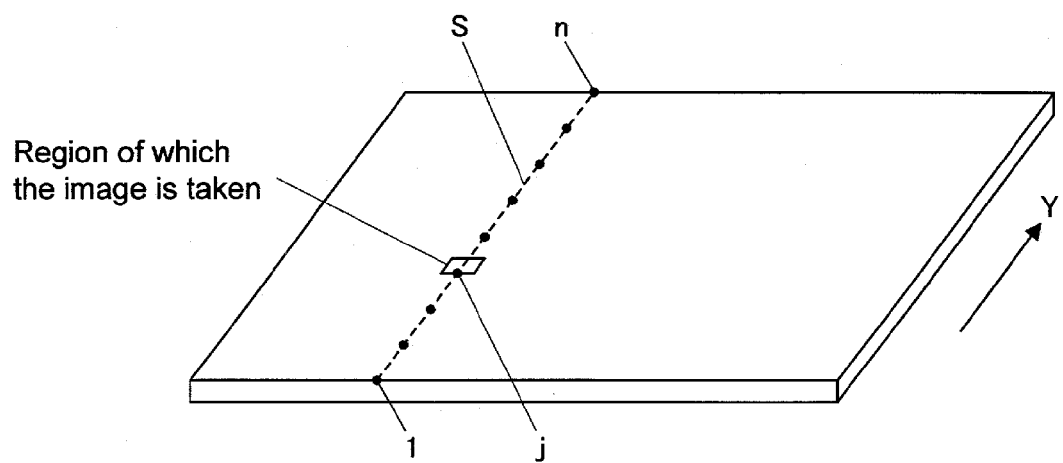
FIGS. 3(a) and 3(b) are diagrams showing the step of determining the location of a trench from the image data that has been taken.
Figure 3B:
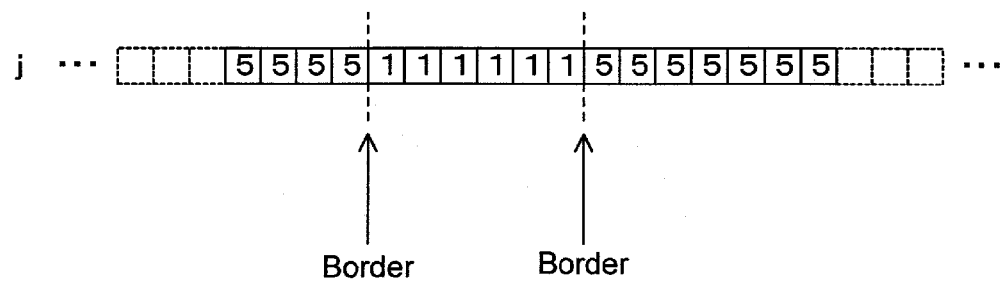

FIGS. 3(a) and 3(b) are diagrams for illustrating a process in which the standard line determining unit determines the location of the trench S on the basis of the image data of the images that have been taken. Here, there are n image taking points along the trench S where images are taken. In addition, the infrared ray line scanning camera 16 can gain image data where a number of pixels (64 pixels, for example) are aligned in the X direction in a single shot.

When the table 1 on which the product W is placed is moved in the Y direction, the respective image taking points 1 to n along the trench S in FIG. 3(a) move through the region of which the image is taken by the infrared ray line scanning camera 16, and thus, images are taken sequentially. FIG. 3(b) schematically shows an example of the image data at the point j from among the image taking points where the numeric value of each pixel indicates the brightness value.

As shown in FIG. 2, infrared rays for imaging, which are included in the light from the illumination L and have a wavelength of 1.4 µm or greater, transmit through the light absorbing layers 13 and 14 in the product W so that part of the infrared rays for imaging reach the Mo electrode layer 12, and thus, part of the infrared rays for imaging reach the trench S created in the Mo electrode layer 12. Part of the infrared rays for imaging that have reached the Mo electrode layer 12 are absorbed by the Mo electrode layer 12, and other parts are reflected and then again transmit through the light absorbing layers 13 and 14 as radiation infrared rays so as to be emitted upwards from the product W. Meanwhile, almost no radiation infrared rays are emitted from the trench S.

Thus, the infrared ray line scanning camera 16 provided above the product W detects the radiation infrared rays.

In general, the radiation ratio of infrared rays differs depending on the material and the state of the surface. The vapor deposited Mo layer has a smooth surface, and the vapor deposited glass also has a smooth surface. In this case, the amount of radiation (radiation ratio) from the surface of the Mo layer is different than that from the surface of the trench S (exposed glass surface) by several times.

Therefore, the difference in the amount of radiation can be clearly detected as the brightness value when an image of the vicinity of the trench S is taken by the infrared ray line scanning camera 16, and thus, the trench S can be detected as image data (brightness data).

That is to say, the amount of radiation from the location corresponding to the trench S is small, which makes the brightness value low, and the amount of radiation from the location of the lower electrode layer (Mo electrode layer) 12 is greater than that, which makes the brightness value higher.

In FIG. 3(b), the brightness value 1 corresponds to the trench S and the brightness value 5 corresponds to the lower electrode. In addition, the portions through which the brightness value changes greatly between adjacent pixels form a border, and therefore, two points, left and right, across which the brightness value changes greatly can be sampled as the locations of the borders so that the width (position) of the trench S can be found. The left and right border locations can be found from each piece of image data from the image taking point 1 to the image taking point n, and the center of the trench S can be determined by connecting the middle points. In reality, the line formed by connecting the middle points is not a complete line due to the microscopic unevenness in the width of the trench resulting from the vibration effects or respective pulses in the laser scribing process using a pulse laser, and thus, an approximation is calculated. The vibration effects are removed in a digital filtering process, or a statistic process, such as an averaging process for determining a line that seems to be most probable, is carried out, for example, so that the location along the center of the trench S is determined as the line that corresponds to the location of the trench S, and this can be set as the standard line for creating a trench M1.

After the standard line has been determined in this manner, the apparatus for creating a trench is adjusted so that the scribing head 8 moves in parallel along this line, and thus, the trench M1 that is parallel to the trench S can be created.

Concretely, the table 1 is rotated until the standard line becomes parallel to the Y direction in the apparatus A for detecting a trench created in a thin film solar cell, and after this adjustment, the trench creating tool 9 is operated for scribing so that a scribing process can be carried out to create a trench that is parallel to the standard line. Alternatively, instead of rotating the table 1, the movement of the scribing head 8 in the X direction and the movement of the table 1 in the Y direction are linked through the control by the control unit so that a scribing process can be carried out in a diagonal direction, which is parallel to the standard line.

Here, it is necessary to create the trench M1 so that not only is the trench M1 parallel to the trench S, but also the distance between the trenches is of a designed value. In order to do so, the infrared ray line scanning camera 16 and the trench creating tool 9 need to be positionally related to each other so that the blade of the trench creating tool 9 can move to the location in which the trench M1 is created according to the design. The infrared ray line scanning camera 16 and the trench creating tool 9 are positionally related to each other in advance by allowing the infrared ray line scanning camera 16 to take an image of the standard line on a standard scale substrate on which a standard line and scales for measuring the distance from the standard line are notched. Next, an actual trench is created through scribing on the standard scale substrate by means of the trench creating tool 9 that has been moved to the starting point of creating a trench, and then, the distance between the standard line and the created trench line is measured using the scale on the standard scale substrate so that the measured distance is set in the apparatus for detecting a trench created in a thin film solar cell for the positional relationship.

Next, the entire manufacturing process for a thin film solar cell according to the present invention is described. FIGS. 4(a) to 4(f) are diagrams showing the manufacturing process for a thin film solar cell.

Figure 4A:
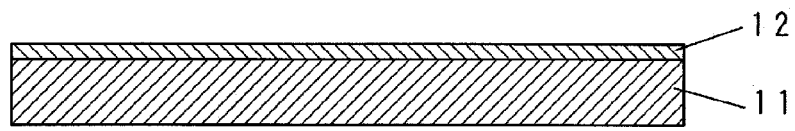
FIGS. 4(a) to 4(f) are diagrams showing the manufacturing steps to which the method for detecting a trench created in a thin film solar cell according to the present invention has been applied.
Figure 4B:
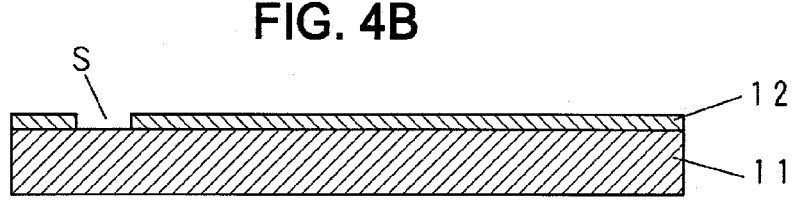

First, as shown in FIG. 4(a), an Mo electrode layer 12 that becomes a lower electrode on the plus side is formed on an insulating substrate 11 made of soda lime glass (SLG) or the like in accordance with a vapor deposition method or a sputtering method. Next, as shown in FIG. 4(b), a trench S for separating the lower electrode layer is created in the Mo electrode layer 12 through scribing by means of the trench creating tool 9 (see FIG. 1). As described above, the trench S can be created through laser scribing using a laser beam.

Figure 4C:
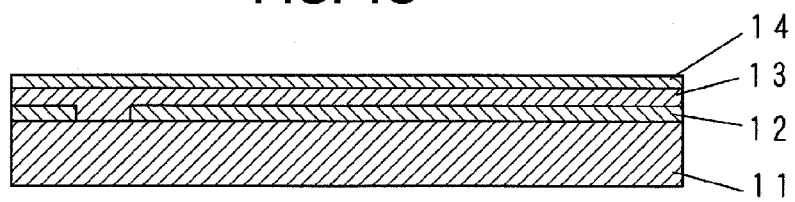

Next, as shown in FIG. 4(c), a light absorbing layer 13 made of a compound semiconductor (CIGS) thin film is layered on top of the Mo electrode layer 12 in accordance with a vapor deposition method or a sputtering method. A buffer layer 14 made of a ZnS thin film or the like for a heterojunction is formed on top of the light absorbing layer 13 in accordance with a chemical bath deposition method (CBD method) so as to be part of the light absorbing layer.

Figure 4D:
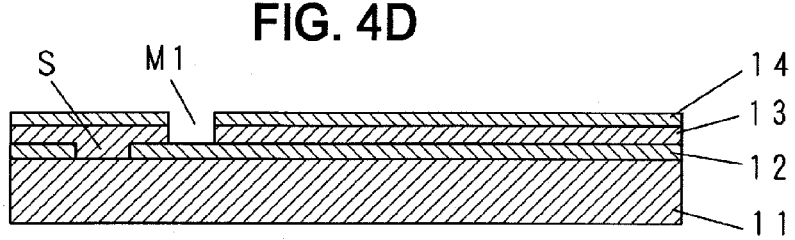
Figure 4E:
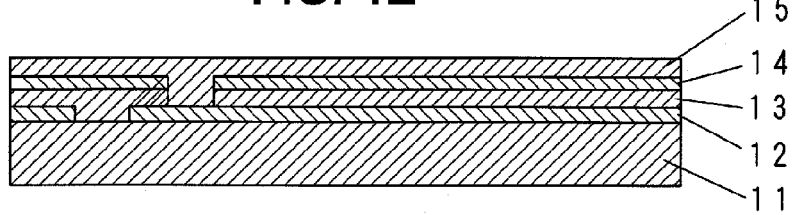
Figure 4F:
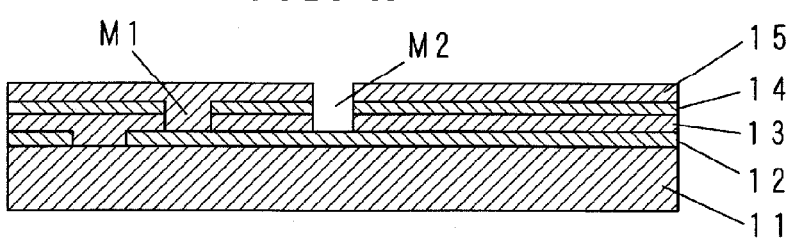
Figure 5A:
FIGS. 5(a) to 5(c) are schematic diagrams showing the manufacturing steps for a conventional thin film solar cell.
Figure 5B:
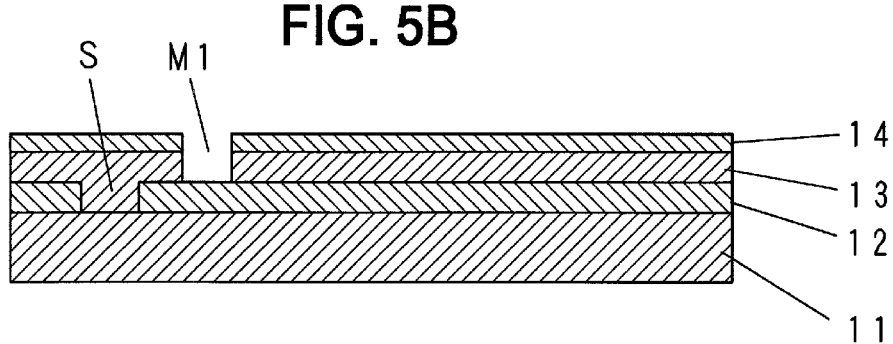
Figure 5C:
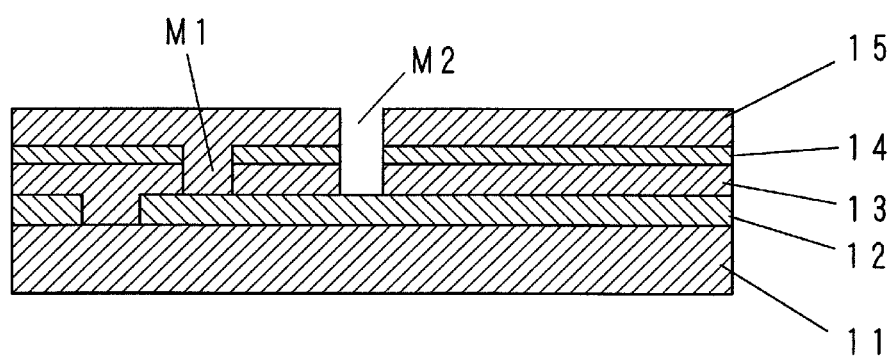

Next, as shown in FIG. 4(d), in the light absorbing layer 13 including the buffer layer 14, a trench M1 for interelectrode contact is created by means of the trench creating tool 9 so as to reach the Mo electrode layer 12 in a location parallel to and away from the trench S for separating the lower electrodes by a predetermined distance in the lateral direction. Prior to this, the above-described infrared ray line scanning camera (infrared ray imaging apparatus) 16 scans the trench S in the Mo electrode layer 12 along the direction of the trench so as to detect the location of the trench S, and on the basis of this, the location in which the trench M1 is to be created, that is to say, the point at which the trench creating tool 9 scribes and the direction in which the scribing progresses (angle), is determined.

Therefore, the trench creating tool 9 is moved so as to maintain this distance and the direction (angle), and thus, the trench M1 is created in the light absorbing layer 13.

As a result, the location and the direction of the trench S in the Mo electrode layer 12 that is located beneath the light absorbing layer 13 can be precisely measured from above by means of the infrared ray line scanning camera 16 even though the trench S cannot be seen with visible light from above the light absorbing layer 13. Therefore, the location and the direction of the trench S can be used as the standard for creating the trench M1 in the light absorbing layer 13 so that the trench M1 is precisely parallel to the trench S, and thus, the loss in the area of the power generation region can be reduced.

Next, as shown in FIG. 4(*e*), a transparent electrode layer 15 made of a ZnO:Al thin film is formed on top of the buffer layer 14 as an upper electrode so as to provide a solar cell substrate having all the functional layers required for power generation using photoelectric conversion. Subsequently, a trench M2 for electrode separation is created through scribing by means of the trench creating tool 9 so as to reach from the transparent electrode layer 15 to the Mo electrode layer 12 beneath.

When this trench M2 is created, it is possible to see the trench M1 that had been created in advance from above the transparent electrode layer 15 because the transparent electrode layer 15 allows visible light to transmit. Accordingly, a camera that can sense visible light is provided above the transparent electrode layer 15, though not shown, and detects the location of the trench M1. Using this trench M1 as the standard, the trench creating tool 9 is moved parallel to the trench M1 while maintaining the set distance from the trench M1, and thus, the trench M2 can be created precisely in the set location.

Though typical embodiments of the present invention are described above, the present invention is not necessarily limited to the above-described embodiments. For example, it is possible to create the trench M1 and the trench M2 in accordance with a laser scribing method using a laser beam in place of the above-described trench creating tool 9.

In addition, though the infrared ray line scanning camera 16 is described as the infrared ray imaging apparatus, an infrared ray two-dimensional camera may be used in place of this. In this case, a process is possible in such a manner that a number of line scanning cameras are aligned. Other improvements and modifications of the present invention are possible as long as an object thereof is achieved and the scope of the claims is not deviated from.

INDUSTRIAL APPLICABILITY

The present invention can be applied to the manufacture of a integrated thin film solar cell using a compound semiconductor film.

EXPLANATION OF SYMBOLS

A Scribing apparatus
S Trench for separating lower electrodes
M1 Trench for inter-electrode contact
M2 Trench for separating electrodes
W Solar cell substrate
1 Table
8 Scribing head
9 Trench creating tool
11 Insulating film
12 Mo electrode layer (lower electrode layer)
13 Light absorbing layer
14 Buffer layer
15 Transparent electrode layer
16 Infrared ray line scanning camera (infrared ray imaging apparatus)
20 Control unit
21 Standard line determining unit

What is claimed is:

1. A method for creating a trench in a product for a thin film solar cell, the product comprising a substrate, a lower electrode layer and a light absorbing layer which are layered in this order, and including a first trench in the lower electrode for separating the lower electrode, the light absorbing layer covering the lower electrode layer and the trench, the method comprising the steps of:

receiving infrared rays from the product to obtain brightness data from an area of the product including the first trench by an infrared camera which cannot detect visible light but detects infrared rays having a wavelength which passes through the light absorbing layer and is located on a side from which the first trench is formed and above the light absorbing layer, the area having a width greater than that of the first trench, the brightness data representing a radiation intensity distribution of the infrared rays from the area, determining borders of the first trench in the area from the brightness data, determining a position and a direction of a baseline to form a second trench in the product in relation to the borders of the first trench, and forming the second trench in the product.

2. The method according to claim 1, wherein the infrared camera is configured to detect infrared rays with a wavelength of 1.4 µm or greater.

3. The method according to claim 1, wherein the infrared camera is an infrared ray line scanning camera to scan the area of the product.

4. The method according to claim 1, wherein the infrared camera is configured to detect infrared rays from the product a plurality of times along the first trench to cover the area.

5. An apparatus for creating a trench in a product for a thin film solar cell, the product comprising a substrate, a lower electrode layer and a light absorbing layer which are layered in this order, and including a first trench in the lower electrode for separating the lower electrode, the light absorbing layer covering the lower electrode layer and the trench, the apparatus comprising:

a table on which the product is placed with the light absorbing layer facing up;

a drive mechanism configured to move the table;

an infrared camera disposed on a side from which the first trench is formed and above the light absorbing layer, the infrared camera being configured not to detect visible light but to detect infrared rays having a wavelength which passes through the light absorbing layer, the infrared camera receiving infrared rays from the product to obtain brightness data from an area of the product including the first trench, the area having a width greater than that of the first trench, the brightness data representing a radiation intensity distribution of the infrared rays from the area; and a controller configured to:
determine borders of the first trench in the area from the brightness data;
determine a position and a direction of a baseline to form a second trench in the product in relation to the borders of the first trench, and control a process tool to form the second trench in the product.

6. The apparatus according to claim 5, wherein the infrared camera is configured to detect infrared rays with a wavelength of 1.4 μm or greater.

7. The apparatus according to claim 5, wherein the infrared camera is an infrared ray line scanning camera to scan the area of the product.

8. The apparatus according to claim 5, wherein the infrared camera is configured to detect infrared rays from the product a plurality of times along the first trench to cover the area.

* * * * *